US00PP33984P2

(12) United States Plant Patent
Miner et al.

(10) Patent No.: US PP33,984 P2
(45) Date of Patent: Mar. 1, 2022

(54) ***LOMANDRA* PLANT NAMED 'KM-MG24'**

(50) Latin Name: *Lomandra longifolia*
Varietal Denomination: KM-MG24

(71) Applicants: Keith Miner, Foresthill, CA (US); Jennifer Miner, Reno, NV (US)

(72) Inventors: Keith Miner, Foresthill, CA (US); Jennifer Miner, Reno, NV (US)

( * ) Notice: Subject to any disclaimer, the term of this patent is extended or adjusted under 35 U.S.C. 154(b) by 0 days.

(21) Appl. No.: 17/318,505

(22) Filed: May 12, 2021

(51) Int. Cl.
*A01H 6/12* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Penny J. Aguirre

(57) ABSTRACT

A new cultivar of *Lomandra longifolia* plant named 'KM-MG24' that is characterized by its foliage that is bright gold in color and its weeping plant habit.

2 Drawing Sheets

Botanical classification: *Lomandra longifolia.*
Varietal denomination: 'KM-MG24'.

BACKGROUND OF THE INVENTION

The present invention relates to a new and distinct cultivar of *Lomandra longifolia* and will be referred to hereafter by its cultivar name, 'KM-MG24'. 'KM-MG24' is a new evergreen perennial grown for container and landscape use.

The Inventors discovered the new cultivar March of 2015 as a naturally occurring chimeral mutation of unnamed and unpatented plant of *Lomandra longifolia* that was growing outdoors in a landscape garden in Sacramento, Calif.

Asexual propagation of the new cultivar was first accomplished by division the direction of the Inventors in May of 2018 in Lincoln, Calif. Asexual propagation by division and tissue culture using meristem tissue has determined that the characteristics are stable and are reproduced true to type in successive generations.

SUMMARY OF THE INVENTION

The following traits have been repeatedly observed and represent the characteristics of the new cultivar. These attributes in combination distinguish 'KM-MG24' as a distinct cultivar of *Lomandra.*

1. 'KM-MG24' exhibits foliage that is bright gold in color.
2. 'KM-MG24' exhibits a weeping plant habit.

The parent plant of 'KM-MG24' differs from 'KM-MG24' in having green foliage. 'KM-MG24' can be most closely compared to *Lomandra longifolia* varieties 'Breeze' (U.S. Plant Pat. No. 15,420) and 'Lime Tuff' (U.S. Plant Pat. No. 23,034). Both 'Breeze' and 'Lime Tuff' are similar to 'KM-MG24' in having a clumping growth habit and in leaf shape and size. 'Breeze' differs from 'KM-MG24' in having green foliage and a much less pronounced weeping habit. 'Lime Tuff' differs from 'KM-MG24' in having leaves that are green in color and stiff upright leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption if applicable under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics the new *Lomandra* as grown outdoors in a 12-inch container in Sacramento, Calif.

The photograph in FIG. 1 provides a side view of the plant habit and appearance of 'KM-MG24'.

Figure 1:
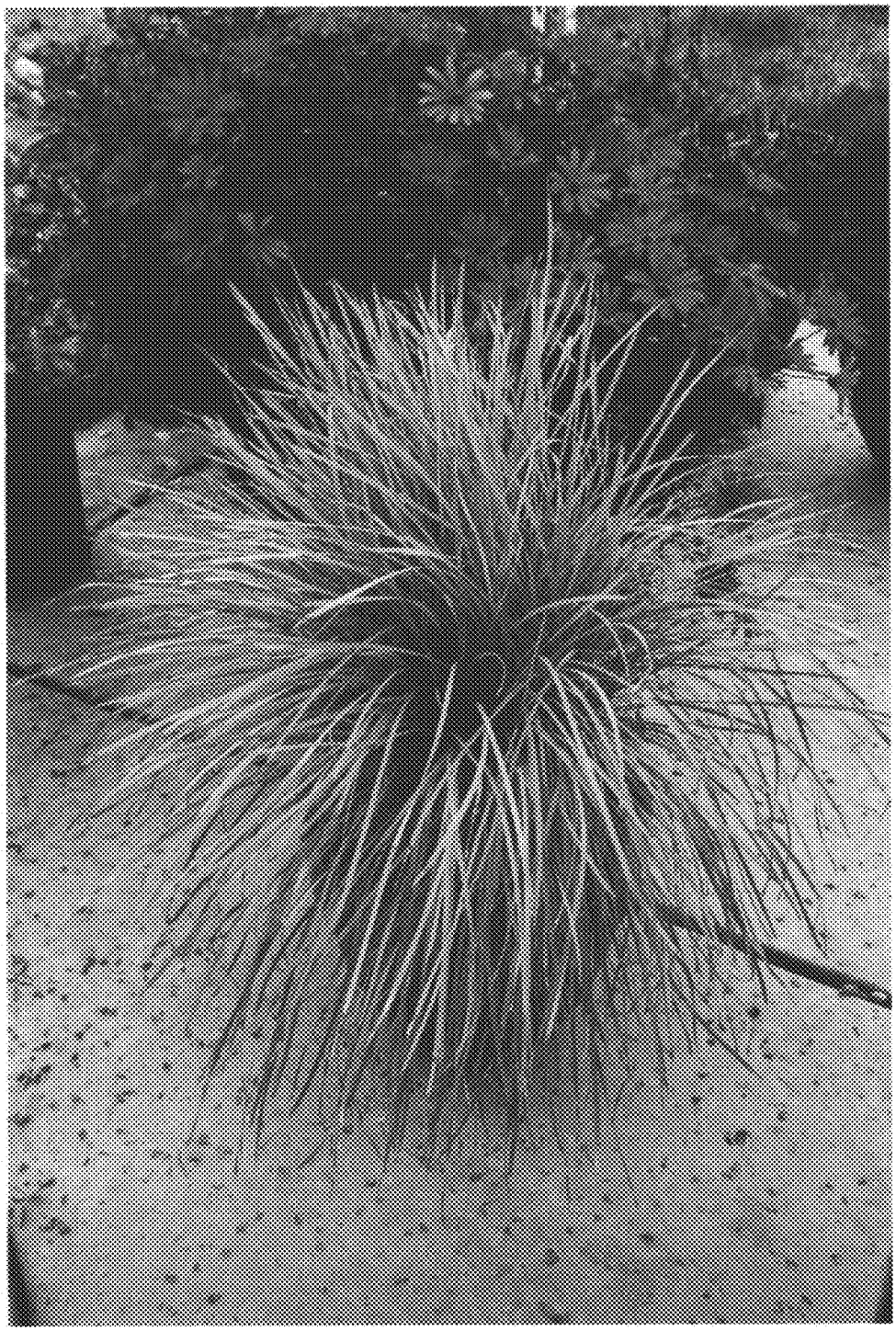
Figure 2:
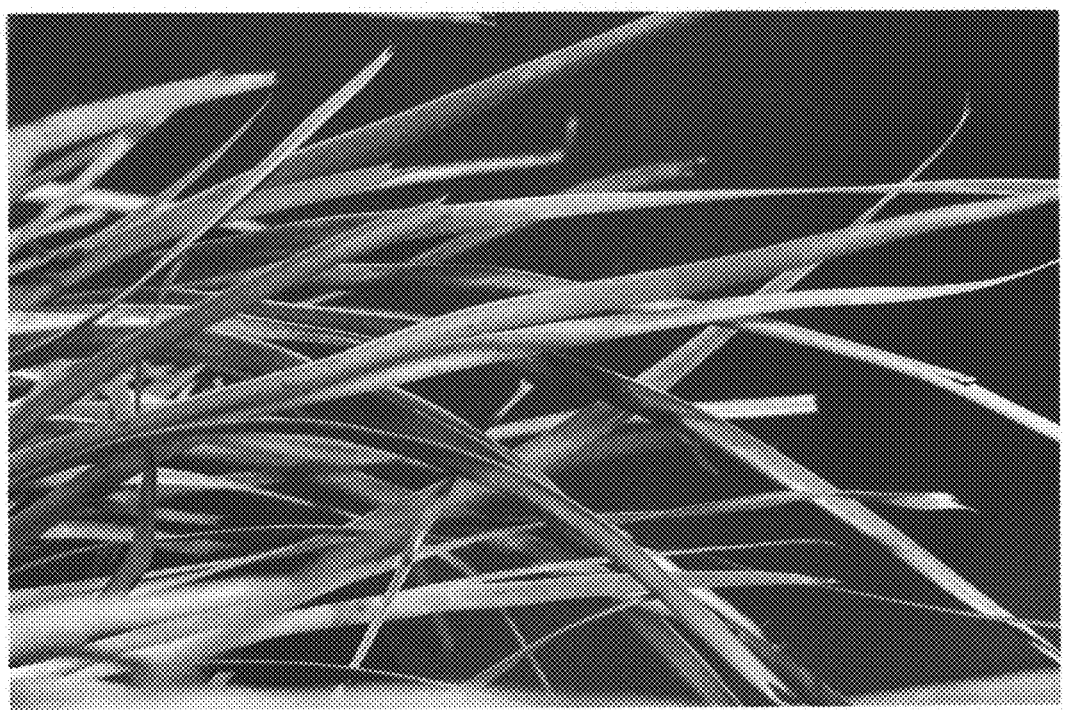

The photograph in FIG. 2 provides a close-up view of the foliage of 'KM-MG24'.

The colors in the photographs may differ slightly from the color values cited in the detailed botanical description, which accurately describe the colors of the new *Lomandra.*

DETAILED BOTANICAL DESCRIPTION

The following is a detailed description of plants of the new cultivar about 15-month-old in age as grown outdoors in 1-gallon containers in Waltsonville, Calif. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Inconspicuous blooms appear in late summer in California.

*Plant type.*—Evergreen perennial, grass-like appearance.

*Plant habit.*—Compact, arching narrow leaves.

*Height and spread.*—50 cm in height and 76 cm in diameter in the landscape.

*Hardiness.*—At least in U.S.D.A. Zones 8 to 10.

*Diseases and pests.*—No susceptibility or resistance to pests and diseases has been observed.

*Root description.*—Fibrous roots are thick and tuberous NN155D in color, fine roots are thin and 156D in color.

*Propagation.*—Tissue culture and division.

*Root development.*—16 to 18 weeks to produce a young plant from rooted tissue culture plantlet.

*Growth rate.*—Moderate.

Foliage description:

*Leaf shape.*—Linear.

*Leaf division.*—Simple.

*Leaf base.*—Sheathing.

*Leaf apex.*—Long acuminate.

*Leaf aspect.*—Center leaves ranging between vertical and slightly arching, surrounding leaves initially emerge upright, then cascade outward and finally arching downward.

*Leaf venation.*—None.

*Leaf margins.*—Entire, smooth.

*Leaf size.*—Average of 17 cm in length and 4 mm in width.

*Leaf number.*—Average of 300 leaves per plant.

*Leaf arrangement.*—Opposite.

*Leaf strength.*—Bendable and very strong.

*Leaf surface.*—Both surfaces slightly glossy and becoming mostly matte as the leaves mature.

*Leaf color.*—Young and mature inner and outer surfaces; 7A, 10A and 143A.

*Leaf sheathes.*—Average of 2 cm in length, 5 mm in width, surface color matches leaf color description of base, margins of sheathes are transparent, thin and paper-like, NN155A in color.

Flower description:

*General description.*—Panicle of clusters of male flowers, not conspicous as the blooms are held within the foliage.

*Inflorescence size.*—Panicle is an average of 8 cm in height and up to 3 cm in width, clusters; an average of 1 mm in depth and 5 mm in diameter.

*Flower quantity per inflorescence.*—Average of 7 clusters per panicle, 3 flowers per cluster.

*Lastingness of inflorescence.*—Flowers last an average of 10 days before drying, persistent.

*Fragrance.*—None.

*Flower buds.*—Oval in shape, average of 2 mm in diameter, 161C in color.

*Flower size.*—Average of 5 mm in length and 2 mm in width.

*Flower shape.*—Closed campanulate.

*Flower color.*—A blend of 155B, and 162A on inner and outer surface of tepals.

*Bracts.*—Average of 1.2 cm in length (including spike), 145A, triangular in shape, truncate base, apex is a spike an average of 3 cm in length but can reach 5 cm in length, smooth surfaces.

*Peduncle.*—Rachis; up to 1.5 cm in length and 2 mm in diameter, upright strong, secondary peduncles; an average of 2 mm in length an 0.75 mm in width, held at a about 20° to vertical, 145A in color.

*Pedicel.*—None, flowers sessile to peduncle.

Reproductive organs:

*Gynoecium.*—None, male flowers only.

*Androecium.*—6 stamens, average of 0.4 mm in length with anther 158A in color, pollen not observed.

*Fruits and seeds.*—Male flowers only, no seed is produced.

It is claimed:

1. A new and distinct cultivar of *Lomandra* plant named 'KM-MG24' as herein illustrated and described.

* * * * *